(12) United States Patent
Dear et al.

(10) Patent No.: US 8,110,371 B2
(45) Date of Patent: Feb. 7, 2012

(54) IDENTIFYING ORGAN DAMAGE

(75) Inventors: James Dear, Edinburgh (GB); David John Webb, Edinburgh (GB)

(73) Assignee: The University Court of the University of Edinburgh (GB)

( * ) Notice: Subject to any disclaimer, the term of this patent is extended or adjusted under 35 U.S.C. 154(b) by 0 days.

(21) Appl. No.: 12/675,479

(22) PCT Filed: Aug. 29, 2008

(86) PCT No.: PCT/GB2008/002947
§ 371 (c)(1),
(2), (4) Date: Oct. 29, 2010

(87) PCT Pub. No.: WO2009/027703
PCT Pub. Date: Mar. 5, 2009

(65) Prior Publication Data
US 2011/0039276 A1    Feb. 17, 2011

(30) Foreign Application Priority Data
Aug. 29, 2007 (GB) .................................. 0716804.0

(51) Int. Cl.
*G01N 33/53* (2006.01)
(52) U.S. Cl. ........................................... 435/7.1; 436/85
(58) Field of Classification Search ........................ None
See application file for complete search history.

(56) References Cited

U.S. PATENT DOCUMENTS

| 6,719,969 | B1 * | 4/2004 | Hogaboam et al. | 424/85.2 |
| 7,469,185 | B2 * | 12/2008 | Mendrick et al. | 702/19 |
| 2004/0053309 | A1 * | 3/2004 | Holt et al. | 435/6 |

* cited by examiner

*Primary Examiner* — Jacob Cheu
(74) *Attorney, Agent, or Firm* — Schwegman, Lundberg & Woessner, P.A.

(57) ABSTRACT

The present invention provides methods for identifying whether or not a patient has, or is at risk of developing drug induced organ damage and methods of treating patients having drug induced organ damage. In particular, the invention relates to a method for identifying whether or not a patent has, or is at risk of developing paracetamol induced liver damage.

13 Claims, 7 Drawing Sheets

A     B     C     D     E

A-   A+   B-   B+   C-   C+   D-   D+

US 8,110,371 B2

IDENTIFYING ORGAN DAMAGE

RELATED APPLICATIONS

This application is a nationalization under 35 U.S.C. 371 of PCT/GB2008/002947, filed Aug. 29, 2008 and published as WO 2009/027703 A2 on Mar. 5, 2009, which claimed priority under U.S.C. 119 to United Kingdom Application No.: 0716804.0, filed on Aug. 29, 2007, which applications and publication are incorporated herein by reference and made a part hereof.

FIELD OF THE INVENTION

The present invention provides methods for identifying whether or not a patient has, or is at risk of developing drug induced organ damage and methods of treating patients having drug induced organ damage. In particular, the invention relates to a method for identifying whether or not a patent has, or is at risk of developing paracetamol induced liver damage

BACKGROUND

A biomarker is a biological characteristic that is measured and evaluated objectively as an indicator of normal biologic processes, pathogenic processes, or pharmacologic response to therapeutic intervention (Hewitt et al., 2004) The identification of clinically useful, validated, protein biomarkers in biological fluids is a major goal for proteomics as this would allow for the earlier detection and reclassification of a wide range of pathological disorders. The proteome of body fluids is complex (Anderson and Anderson, 2002) and proteomics on these fluids is challenging as the more abundant proteins, for example albumin in plasma and Tamm-Horsfall Protein (THP) in urine, are more likely to be detected and the less abundant, and more interesting and informative proteins are difficult to identify.

Multiple organ injury has high mortality and there is a need to understand the pathological nature of how the organ injury arises. Drug overdose (for example paracetamol overdose) can induce multiple organ failure and a key mediator of paracetamol induced organ injury is the transcription factor c-Jun.

Deliberate or accidental overdose with paracetamol (also known as acetoaminophen—APAP) is the most common cause of poisoning in the United Kingdom. For example, around 1 person per day requires admission to the Royal Infirmary of Edinburgh for treatment of a significant APAP overdose (unpublished data). However, only around 12% of admissions will develop any degree of organ injury and only around 50 patients per year from all of Scotland are referred to the Scottish Liver Transplant Unit with severe APAP—induced liver injury (unpublished data). APAP overdose is treated with a glutathione pro-drug (N-acetylcysteine (NAC)) but adverse reactions to this antidote are common (around 15% of patients). As the majority of patients will not develop organ injury we may be over-treating with a potentially toxic antidote.

The need for NAC treatment is determined by the blood paracetamol concentration. Those found to have a sufficiently high concentration of paracetamol in their blood are administered NAC intravenously over a period of approximately 20 hours. Once the NAC treatment is complete, further tests to assess the extent of any liver damage are conducted. These tests require the measurement of serum transaminase enzymes (ALT and AST), blood clotting (INR) and serum creatinine. As such, paracetamol induced organ damage may, at present, only be excluded after a minimum period of 20 hours.

In addition, adverse reaction to NAC are common and as such it is desirable to reduce the length of NAC infusion.

Existing biomarkers of APAP-induced organ injury (for example serum alanine transaminase (ALT), international normalized ratio (INR) and creatinine) do not accurately detect or exclude injury until around 24 hours post-APAP ingestion. If we could detect or exclude injury earlier then we could reduce the number and/or length of hospital admissions.

The ability of eukaryotic cells to release components of their cell membrane was first described by Wolf in 1967 and eloquently termed 'platelet dust'. Essentially all cell types release small membrane vesicles, today known as microparticles or exosomes, especially when the cells are activated or during apoptosis (George et al., 1982).

The urinary proteome is easier to investigate than blood and large amounts can be collected. All nephron segments of the kidney normally secrete small vesicles containing apical membranes and intracellular fluid into the urine and these vesicles, termed exosomes, are less than 80 nm in size (Johnstone et al., 1987). Exosomes are orientated 'cytoplasmic-side inward' which is a unique characteristic of these vesicles. Exosomes can be isolated from urine by differential centrifugation and several renal disease-related proteins have been identified in these exosomes through liquid-chromatography-tandem mass spectrometry (LC-MS/MS) (Pisitkun et al., 2004). Zhou et al. (2006) established the optimal conditions for the collection and storage of urine exosomes to maximise the amount of exosomal protein that can be isolated and, therefore, facilitate protein identification. Urinary exosomes could provide key biomarkers of renal disease as their numbers and composition could be altered during disease and may give an indication of organ dysfunction. It should be noted, however, that urinary exosomes might reflect changes in circulating blood MPs as well as changes in kidney function. Therefore, urinary exosomal protein may represent a source of biomarkers for systemic disease. The ability to isolate and characterise urine exosomes may be the first step in identifying disease biomarkers.

It is among the objects of the present invention to obviate or mitigate the abovementioned problems with the prior art.

SUMMARY OF THE INVENTION

The present invention is based upon the observation that patients who have taken or who have been administered an incorrect or inappropriate dose of a drug or drugs, show elevated levels of protein in their bodily fluids. Furthermore, the level of protein present in a bodily fluid may indicate that the patient has, or is at risk of developing drug induced organ damage.

Thus, in a first aspect, the present invention provides a method of identifying whether a patient has, or is at risk of developing drug induced organ damage, said method comprising the steps of;

(a) providing a sample from a patient; and (b) identifying a level of protein in said sample;

wherein an increase in the level of protein indicates that the patient has, or is at risk of developing drug induced organ damage.

The term "patient" may be taken to encompass those known to have, or suspected of having taken, or been administered, an inappropriate or incorrect dose of a drug. Furthermore, while a "patient" may show clinical signs of damage to one or more organs, they may also be asymptomatic and/or at risk of developing drug induced organ damage. As such, the present invention aims to provide a method capable of identifying (or predicting) whether or not a patient has, or is at risk of developing organ failure and which may assist in the determination of whether that patient requires further treatment.

It is to be understood that the term "drug" may relate to any compound or combination of compounds used in the diagnosis, treatment or prevention of a disease or condition. Such compounds may otherwise be known as types of medication or medicines. Additionally, or alternatively, the term "drug" may relate to other types of compound administered to, or taken by, a subject in order to alter behaviour, consciousness and/or perception. Such compounds may include, for example, narcotics, such as alcohol, heroin and/or hallucinogens such as LSD.

By way of example, the present method may be used to identify instances of organ damage induced by, for example, drugs such as antibiotics and/or anti-inflammatory, antipyretic, analgesic and/or chemotherapeutic agents. In one embodiment, the present invention may be used to identify instances of organ damage induced by antipyretic/analgesic drugs such as paracetamol (N-(4-hydroxyphenyl)ethanamide).

It is important to note that drug induced organ damage can take many hours to develop and, in some cases, although an incorrect or inappropriate dose of a drug has been taken by, or administered to a patient, organ damage requiring further treatment may not ensue. Nevertheless, current protocols often demand that patients suspected of having, or known to have taken an inappropriate/incorrect dose of a drug or drugs, are treated and hospitalised for a period of observation. Such patients are only discharged once doctors are sure no further treatment is required. As such, one of skill will appreciate that in many cases the observation period proves to have been unnecessary as the drug taken by the patient did not result in organ damage requiring further treatment. These unnecessary periods of hospitalisation are a considerable drain on the limited resources available to medical staff.

As stated, symptoms indicative of drug induced organ damage may take a considerable period of time to become apparent and while damage to one or more organs may have occurred, the patient may appear asymptomatic. For example, it is possible for a patient to have damaged a portion of an organ, such as the liver, but not show any symptoms or clinical signs of the damage.

In view of the fact that the symptoms of drug induced organ damage may take a considerable period of time to develop, at this moment in time, hospitalisation and periods of observation are essential.

Accordingly, the present invention provides a method capable of rapidly establishing and/or predicting whether or not a patient, suspected of being administered or having taken an inappropriate or incorrect dose of a drug or drugs, has sustained damage to one or more organs and whether that patient is likely to require further treatment. In this way, the numbers of patients hospitalised for unnecessary periods of observation may be drastically reduced.

In one embodiment, the present invention provides a method of identifying whether a patient has, or is at risk of developing paracetamol induced organ damage, said method comprising the steps of;
(a) providing a sample from a patient; and
(b) identifying a level of protein in said sample;
wherein an increase in the level of protein indicates that the patient has, or is at risk of developing paracetamol induced organ damage.

Drug induced organ damage may result from the toxic effects of the drug itself or a metabolite thereof. Additionally, or alternatively, organ damage may result from an uncontrolled and/or inappropriate inflammatory response initiated by the drug(s) or a metabolite or metabolites thereof.

Drug induced organ damage usually results from the administration of an incorrect or inappropriate dose and typically the incorrect or inappropriate dose represents an overdose. As such, each of the methods described herein may be used to identify instances of organ damage resulting from drug, for example paracetamol, overdose (may otherwise be referred to as drug "poisoning").

The term "organ damage" as used herein, may be defined as the loss of function and/or necrosis of one or more cells comprising the organ and may affect one or more of the lungs, heart, kidneys, liver, pancreas, brain, stomach, intestine (small and/or large) and/or genitor-urinary or haematopoietic systems. In severe cases of drug induced organ damage, approximately 50%-90% of the cells comprising the organ may loose function or die.

By way of example, drug induced liver damage may be characterised by the loss of function and/or necrosis of one or more hepatocytes resulting in, for example, total or partial loss of liver function. While a partial loss of liver function may not result in any detectable or identifiable symptoms, in some cases damage to the liver may manifest as jaundice and/or the development of hepatic encephalopathy wherein toxic metabolites and compounds normally removed by the liver, accumulate in the blood resulting in damage to the brain.

In some patients, drug induced organ damage may develop or progress into total organ failure wherein the organ ceases to function as it would in a healthy individual. Occasionally, the drug or drugs may damage a number of organs and in instances of severe damage, multiple organ failure (MOF) may result.

In a further embodiment, the present invention provides a method of identifying whether a patient has, or is at risk of developing paracetamol induced liver damage, said method comprising the steps of,
(a) providing a sample from a patient; and
(b) identifying a level of protein in said sample;
wherein an increase in the level of protein indicates that the patient has or is at risk of developing, paracetamol induced liver damage.

One of skill in the art will appreciate that the term "sample" (as used herein) may be a sample of tissue or a biopsy. In addition, the term "sample" may include samples of bodily fluids such as whole blood, plasma, serum, lymph, urine, sweat and saliva and/or tissue and/or gland secretions. For example, and in one embodiment, the sample may comprise a bodily fluid such as whole blood, preferably plasma. In a further preferred embodiment, and rather unexpectedly, the sample may comprise a sample of urine. This represents a surprising finding as one of skill in the art may expect the proteinaceous content of a urine sample only to be indicative of renal health. Accordingly, the discovery that the protein content may also be indicative of the health of other organs, such as the liver, is unexpected. As such, in one embodiment, the present invention provides methods of identifying whether or not a patient has, or is at risk of developing drug induced organ damage, wherein the organ is not the kidney.

The sample referred to herein may be subjected to a protocol capable of isolating microparticles and/or exosomes therefrom. Microparticles and/or exosomes comprise vesicles released by cells. For example, cells of the vascular system—particularly endothelial cells and/or cells comprising organ tissue may release microparticles and/or exosomes. These microparticles and/or exosomes may further comprise various proteins derived from the surface, cytoplasm and/or nucleus of the cells from which they originate.

One of skill in the art will be familiar with the techniques which may be used to isolate microparticles and/or exosomes from samples such as those described above. For example, the sample may be subjected to centrifugation. Advantageously, ultracentrifugation may be used to isolate microparticles and/or exosomes from samples. Additionally or alternatively, microparticles isolated from samples such as blood (and potentially exosomes from urine) may be isolated or sorted into distinct populations (i.e. according to originating cell type (endothelial cell etc)) by cell sorting techniques. By way of example, it may be possible to tag or label the microparticles with one or more agents capable of binding one or more components of the microparticles. In this way the microparticles may be sorted (or isolated) into populations by subjecting the tagged or labelled microparticles to fluorescence activated cell sorting (FACS) analysis. Advantageously, the agents capable of binding one or more components of the microparticles may be antibodies which may be labelled with a detectable moiety (as described below). By way of a specific example, Flourescein isothiocyanate (FITC)-labelled anti-human CD31 and Phycoerythrin (PE)-labelled anti-human CD42b antibody markers may be used to distinguish and or sort distinct populations of microparticle from blood and/or plasma samples.

Accordingly, the methods described herein may comprise the further step of isolating microparticles and/or exosomes from the sample provided by the patient. As such, in a yet further embodiment, the present invention provides a method of identifying whether or not a patient has, or is at risk of developing drug induced organ damage, said method comprising the steps of;

(a) providing a sample from a patient;
(b) isolating microparticles and/or exosomes from said sample; and
(c) identifying a level of protein in said microparticles and/or exosomes;

wherein an increase in the level of protein in said microparticles and/or exosomes indicates that the patient has, or is at risk of developing drug induced organ damage.

Advantageously, immediately after collection and prior to subjecting the sample to the abovementioned microparticle/exosomes extraction protocol, a compound or compounds may be added to the sample to prevent the degradation, denaturation and/or breakdown of the proteinaceous matter of the sample. Such compounds may include, for example, inhibitors of proteinase enzymes—otherwise known as proteinase inhibitors.

In addition to referring to the total protein content of a sample, the term "protein" as used herein, may be taken to mean the level of one or more particular or specific types of protein. For example, it may be possible to identify and/or predict instances of drug induced organ damage by identifying levels of certain cell surface, cellular, cytoplasmic and/or nuclear proteins. As such, each of the methods described herein may rely on the identification of certain cellular, cytoplasmic and/or nuclear proteins. By way of example, the present invention may require the identification of levels certain transcriptions factors, including, for example, c-Jun—a protein transcription factor that can be activated by a mitogen activated protein (MAP) kinases (MAPF). Additionally, or alternatively, the methods described herein may involve the identification of intracellular proteins such as, for example, Cyclophilin A (CyPA—also designated peptidyl-prolyl cis/trans isomerase A or PPIA).

Thus in one embodiment, the present invention provides a method of identifying whether or not a patient has, or is at risk of developing, drug induced organ damage, said method comprising;

(a) providing a sample from a patient; and
(b) identifying a level of a transcription factor and/or an intracellular protein in said sample;

wherein an increase in the level of a transcription factor and/or intracellular protein identified in the sample indicates that the patient has, or is at risk of developing drug induced organ damage.

In one embodiment, the transcription factor is a c-Jun N-terminal kinase (JNK). In a further embodiment the intracellular protein is CyPA.

Without wishing to be bound by theory, it is thought that exposure to drugs, and in particular overdoses of drugs such as, for example, paracetamol, may lead to MAPK activation which in turn activates c-Jun which may lead to an increase in the amount of c-Jun. Furthermore, since drugs such as, for example, paracetamol, cause marked cellular necrosis, it is hypothesised that leakage from injured cells is the most likely source of intracellular proteins such as CyPA in samples such as, urine, blood and the like.

Genes belonging to the c-Jun N-terminal kinase family, encode nuclear proteins associated with transcriptional complexes and c-Jun is the major component of the AP-1 transcription factor, the activity of which is known to be induced by a wide variety of stimuli including, for example, cellular stress. Furthermore, the c-Jun N-terminal kinases consist of ten isoforms deriving from the three genes JNK1, JNK2 and JNK3 and it is to be understood that the present invention relates to methods involving the identification of levels of one or more of these isoforms.

CyPA is an abundant intracellular protein with a number of diverse functions. It is the primary intracellular drug target for the immunosuppressive agent cyclosporine[2] and is a member of the immunophilin class of proteins that possess peptidyl-prolyl cis/trans isomerase activity that is important for intracellular protein folding[3]. CyPA binds HIV[4] and cyclophilin binding drugs have potent anti-HIV activity.

Furthermore, CyPA is released by cells into the extracellular milieu in response to a number of stimuli. Extracellular CyPA is pro-inflammatory, for example it is a chemotactic agent for inflammatory cells[5].

In view of the above, the level of c-Jun identified in a sample, preferably a urine sample (and more preferably exosomes derived therefrom), of a patient known to have, or suspected of having taken a paracetamol overdose may be indicative or predictive of paracetamol induced liver damage.

Similarly, the level of CyPA identified in a sample, preferably a urine sample of a patient known to have or suspected of having taken a paracetamol overdose may be indicative or predictive of paracetamol induced liver damage.

Thus in one embodiment, the present invention provides a method of identifying whether or not a patient has, or is at risk of developing paracetamol induced liver damage, said method comprising the steps of;

(a) providing a urine sample from a patient;
(b) optionally isolating microparticles and/or exosomes from said urine sample; and
(c) identifying a level of the transcription factor c-Jun and/or CypA in said urine sample and/or the microparticles and/or exosomes isolated in step (b);

wherein an increase in the level of c-Jun and/or CypA identified in the urine and/or microparticles and/or exosomes isolated therefrom indicates that the patient has, or is at risk of developing paracetamol induced liver damage.

Typically 10 ng to 10 µg of protein, such as C-Jun and/or CypA per ml of urine may be indicative of liver damage.

One of skill in the art will be familiar with the techniques which may be used in combination with any of the methods of this invention to identify levels of protein, or levels of specific protein(s) in samples such as those described herein. Such techniques include, for example, protein assays, enzyme based assays (see for example Kullertz et al (1998), Clinical Chemistry, 44:3, p502-508) to which the skilled reader is directed and which is incorporated herein and immunological and PCR based techniques such as those described in more detail below.

In order to determine whether or not there is an increased level of protein present in the sample tested, one of skill in the art may compare the results obtained from any of the methods described herein (i.e. the identified level of total and/or specific protein(s)) with the level of protein (either total or specific) present or identified in a reference sample. A "reference sample" may be considered as a sample derived from a healthy subject—i.e. a reference subject, known not to have organ damage (drug induced or otherwise).

Additionally, or alternatively, the results obtained may be compared with a number of reference samples, each having been obtained from a reference subject.

Accordingly, in a further embodiment, the present invention provides a method of identifying whether or not a patient has, or is at risk of developing drug induced organ damage, said method comprising the steps of;
(a) providing a sample from a patient;
(b) identifying a level of protein in said sample; and
(c) comparing the results with the level of protein identified in a reference sample;
wherein an increase in the level of protein identified in the sample relative to the level identified in the reference sample indicates that the person has, or is at risk of developing drug induced organ damage.

Furthermore, the above described method of identifying paracetamol induced liver damage may further comprise the step of comparing the results with those obtained from a reference urine sample provided by a subject known not to have paracetamol induced liver damage.

Additionally, or alternatively, the results obtained from the methods described herein may be compared with those obtained from reference samples intended to represent a patient with different levels of organ damage. One of skill may know such samples as "positive control samples". For example, the results may be compared with the results obtained from samples derived from patients known to have taken an overdose but who have not sustained organ damage, subjects who are asymptomatic but who have sustained damage to one or more organs and/or subjects who, after taking a drug overdose, show symptoms indicative of damage to one or more organs.

Advantageously, the reference sample may also be subjected to the microparticle/exosomes isolation protocols described above.

Preferably, the reference sample should be the same type of sample as the sample provided by the patient. By way of example, if the sample provided by the patient is a urine sample, the reference sample should also be a urine sample.

The level of drug induced organ damage suffered by a subject may be determined by a number of currently available clinical means. Most simply, organ damage and/or failure may be inferred from a clinical need for organ support, for example renal replacement therapy (for example by haemodialysis) or ventilatory support for respiratory failure, or vasopressor support for failure to maintain peripheral vascular resistance. Certain combinatorial scoring systems, for example the multiple organ dysfunction score (Marshall, J. C., Cook, D. J., Christou, N. V., Bernard, G. R., Sprung, C. L. and Sibbald, W. J.: 1995, 'Multiple organ dysfunction score: a reliable descriptor of a complex clinical outcome.' *Crit Care Med* 23, 1638-52.) or the Acute Pyysiology and Chronic Health Evaluation score (Knaus, W. A., Draper, E. A., Wagner, D. P. and Zimmerman, J. E.: 1985, 'APACHE II: a severity of disease classification system.' *Crit Care Med* 13, 818-29), are also informative.

Preferably, an increase of approximately 2 to about 10 fold in the level of protein present in the sample relative to the level present in the reference sample, may be indicative of a level of drug induced organ damage which may not require further treatment. More preferably an increase of approximately 3 to 9 fold or even more preferably a 4 to 8 fold increase in the level of protein identified in the sample relative to the level identified in the reference sample, may be indicative of a level of drug induced organ damage which may not require further treatment. In one embodiment an increase of approximately 5 to 7 fold in the level of protein identified in the sample relative to the level identified in the reference sample, is indicative of a level of drug induced organ damage which may not require further treatment.

In contrast, an increase of approximately 8 to about 100 fold in the level of protein present in the sample relative to the level present in the reference sample may be indicative of drug induced organ damage which requires further treatment. More preferably an increase of approximately 10 to 90 fold or even more preferably 20 to 80 fold increase in the level of protein may be indicative of drug induced organ damage which requires further treatment. In further embodiments an increase of approximately 25 to 85 fold, more preferably 30 to 70 or even more preferably 35 to 65 fold increase in the level of protein may be indicative of drug induced organ damage which requires further treatment.

In addition to providing methods which rely on identifying levels of protein in samples, each of the methods described herein may additionally, or alternatively, require the identification of levels of nucleic acids present in the sample provided. One of skill in the art will appreciate that the level, of nucleic acid present in a sample may be indicative of the level of protein present which in turn may be indicative of drug induced organ damage. Furthermore, it may be possible to determine the level of specific proteins present in a sample by exploiting nucleic acids which encode specific proteins present in the samples described herein. By way of example, it may be possible to identify levels of nucleic acid encoding the transcription factor c-Jun and/or CyPA in the sample provided.

The term nucleic acid is intended to encompass both deoxyribonucleic acid (DNA) and ribonucleic acid (RNA). In the case of RNA, the term may also include mRNA and tRNA. More specifically, and in one embodiment, the present invention may require the identification of a level of RNA, preferably mRNA, present in the sample provided. Advantageously, the mRNA may encode the transcription factor, c-Jun and/or CyPA. Methods which the skilled man may use to identify levels of nucleic acid present in the sample provided are discussed below.

One of skill in the art will be familiar with the techniques which may be used to identify levels of total protein and/or levels of specific proteins in samples such as those listed above. Furthermore, it is to be understood that each of the methods described below should be taken as applicable to each of the methods described herein.

In one embodiment, the level of total protein identified in a sample may be identified by way of a protein assay. Assays such as, for example, the Bradford protein assay are suitable for this purpose. Assays of this type often require the use of standard or reference protein samples which may be prepared using known concentrations of, for example, bovine serum albumin.

In order to identify levels of specific proteins, it may be desirable to use certain immunological techniques, which exploit agents capable of binding proteins. Techniques of this type may be particularly suited to identifying levels of proteins such as, for example, transcription factors such as c-Jun and/or CyPA.

In one embodiment, the present invention may provide a method comprising the step of contacting a substrate (or portion thereof) with a sample to be tested, under conditions which permit the association, interaction, binding and/or immobilisation of a specific protein or proteins, for example transcription factors (such as c-Jun) and/or CyPA present in the sample, to said substrate.

Suitable substrates may include, for example, glass, nitrocellulose, paper, agarose and/or plastics. A substrate such as, for example, a plastic material, may take the form of a microtitre plate.

Alternatively, the substrate to be contacted with the sample to be tested may comprise an agent capable of binding a specific protein or proteins. Preferably, the agent capable of binding the specific proteins, is/are bound to the substrate (or at least a portion thereof). Suitable binding agents may include, for example, antibodies such as monoclonal antibodies or polyclonal antibodies and/or other types of peptide or small molecule capable of binding to specific proteins such as the transcription factor c-Jun and/or CyPA. It is to be understood that this definition applies to all types of binding agent mentioned herein. As such, the substrate (or a portion thereof) may be contacted with the sample to be tested under conditions which permit binding or interaction between the agents capable of binding the specific protein(s) and any of the relevant specific protein present in the sample.

Any specific protein bound to the substrate or agents capable of binding specific protein(s) may be detected with the use of a further agent capable of binding the specific protein(s) (referred to hereinafter as the "primary binding agent"). Additionally, or alternatively, the primary binding agents may have affinity for, or bind to, specific protein:: substrate complexes or complexes comprising specific protein and the abovementioned agents capable of binding specific protein(s).

The primary binding agents may be conjugated to moieties which permit them to be detected (referred to hereinafter as "detectable moieties"). For example, the primary agents may be conjugated to an enzyme capable of reporting a level via a colourmetric chemiluminescent reaction. Such conjugated enzymes may include but are not limited to Horse Radish Peroxidase (HRP) and Alkaline Phosphatase (AlkP). Additionally, or alternatively, the primary binding agents may be conjugated to a fluorescent molecule such as, for example a fluorophore, such as FITC, rhodamine or Texas Red. Other types of molecule which may be conjugated to binding agents include radiolabelled moieties.

Alternatively, any specific protein(s) bound to the substrate or agents capable of binding specific protein, may be detected by means of a yet further binding agent (referred to hereinafter as "secondary binding agents") having affinity for the primary binding agents. Preferably, the secondary binding agents are conjugated to detectable moieties.

The amount of primary binding agent (or secondary binding agent bound thereto) bound to one or more specific proteins, may represent the level of a particular protein or proteins present in the sample tested.

As stated, the immunological methods described herein may be particularly suited to identifying levels of transcription factors such as c-Jun and/or CyPA, the levels of which in a sample provided by a patient suspected of having taken or been administered an inappropriate or incorrect dose of a drug, may indicate drug induced organ damage.

In one embodiment, the above described methods for identifying a level of a specific protein or proteins, may take the form of "dip-stick" test, wherein a substrate (or portion thereof) is contacted with a sample to be tested under conditions which permit the binding of the specific protein(s) (Such as the transcription factor c-Jun and/or CyPA) present in the sample to the substrate or a binding agent bound or immobilised thereto.

In a further embodiment, the methods may take the form of an immunological assay such as, for example, an enzyme-linked immunosorbent assay (ELISA). An ELISA may take the form of a "capture" ELISA wherein, a sample to be tested is contacted with a substrate, and any specific protein(s) present in the sample is/are "captured" or bound by a binding agent (capable of binding the specific protein or proteins) bound or immobilised to the substrate. Alternatively, the sample may be contacted with the substrate under conditions which permit "direct" binding between the specific protein(s) present in the sample and the substrate.

Each of the ELISA methods described above may comprise a "direct" specific protein detection step or an "indirect" identification step. ELISAs involving such steps may be known as "direct" ELISAs or "indirect" ELISAs.

A "direct" ELISA may involve contacting the sample to be tested with a substrate under conditions which permit the binding of any specific protein or proteins present in the sample to the substrate and/or a binding agent bound thereto. After an optional blocking step, bound protein (for example the transcription factor c-Jun and/or CyPA) may be detected by way of an agent capable of binding the specific protein (i.e. a primary binding agent). Preferably, the primary binding agents are conjugated to a detectable moiety.

An "indirect" ELISA may comprise the further step of, after contacting the specific protein or proteins with a primary binding agent, using a further binding agent (secondary binding agent) with affinity or specificity for the primary binding agent. Preferably, the secondary binding agent may be conjugated to a detectable moiety.

Other techniques which exploit the use of agents capable of binding specific proteins and which may be used to identify levels of specific proteins present in samples of bodily fluids, include, for example, techniques such as Western blot or dot blot. A Western blot may involve subjecting a sample to electrophoresis so as to separate or resolve the components, for example the proteinaceous components, of the sample. In one embodiment, the sample to be subjected to electrophoresis may comprise a bodily fluid sample provided by a patient suspected of having taken or been administered an inappropriate or incorrect dose of a drug. In a yet further embodiment, the sample may further comprise or consist of microparticles and/or exosomes obtained from said sample.

The resolved components may then be transferred to a substrate, such as nitrocellulose. In order to identify levels of specific protein(s) such as the transcription factor, c-Jun and/or CyPA present in the sample, the substrate may be contacted with a binding agent capable of binding the specific protein(s) under conditions which permit binding between any of the specific protein(s) present in the sample and the agents capable of binding the specific protein(s).

Advantageously, the agents capable of binding the specific protein(s) may be conjugated to a detectable moiety.

Alternatively, the substrate may be contacted with a further binding agent having affinity for the binding agent capable of binding the specific protein(s). Advantageously, the further binding agent may be conjugated to a detectable moiety.

In the case of a dot blot, the sample or a portion thereof, may be contacted with a substrate such that any proteins, such as the transcription factor c-Jun and/or CyPA present in the sample is/are bound to or immobilised on the substrate. Identification of any bound or immobilised protein may be conducted as described above.

In any of the abovementioned techniques, the amount of primary or secondary binding agent detected is representative of, or proportional to, the amount of one or more specific proteins present in the sample and may be indicative of drug induced organ damage.

In order to detect and/or identify a level of specific protein in a sample, it may also be possible to utilise and enzyme which converts the specific protein into one or more other compounds. Alternatively, where the protein to be detected is an enzyme, it may be possible to contact the sample with a substrate specific for the enzymes such that an enzyme/substrate reaction occurs yielding a product. In both cases, the level of product resulting from the enzyme/substrate reaction, may indicate the level of specific protein present in the sample. By way of example, in order to determine the level of CyPA in a sample, such as a urine sample, derived from a patient thought or known to have taken a paracetamol overdose, the enzymatic activity of CyPA (peptidyl-prolyl cis/trans isomerase activity) may be exploited (see Kullertz et al (1998)).

Other techniques which may be used to identify levels of specific proteins such as the transcription factor, c-Jun or CyPA, include, for example, polymerase chain reaction (PCR) based techniques such as real-time PCR (otherwise known as quantitative PCR). Such a technique may be used to determine whether or not a particular nucleic acid sequence is present in a bodily fluid sample and the level of expression of that nucleic acid.

In the present case, real time-PCR may used to determine whether or not the nucleic acid sequences encoding specific proteins such as c-Jun and CyPA are present in a sample provided and the level of expression of those nucleic acid sequences. Typically, and in order to quantify the level of expression of a particular nucleic acid sequence, reverse transcriptase PCR may be used to reverse transcribe the relevant mRNA to complementary DNA (cDNA). Preferably, the reverse transcriptase protocol may use primers designed to specifically amplify an mRNA sequence of interest. Thereafter, PCR may be used to amplify the cDNA generated by reverse transcription.

Typically, the cDNA is amplified using primers designed to specifically hybridise with a certain sequence and the nucleotides used for PCR may be labelled with fluorescent or radiolabelled compounds.

One of skill in the art will be familiar with the technique of using labelled nucleotides to allow quantification of the amount of DNA produced during a PCR. Briefly, and by way of example, the amount of labelled amplified nucleic acid may be determined by monitoring the amount of incorporated labelled nucleotide during the cycling of the PCR.

Preferably, the results obtained may be compared with those obtained from a reference sample.

Further information regarding the PCR based techniques described herein may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

Other techniques which may be used to determine the level of specific proteins present in a sample include, for example Northern and/or Southern Blot techniques. A Northern blot may be used to determine the amount of a particular mRNA present in a sample and as such, could be used to determine the amount of a specific protein such as the transcription factor, c-Jun and/or CyPA, present in a sample. Briefly, mRNA may be extracted from a sample using techniques known to the skilled artisan, and subjected to electrophoresis. A nucleic acid probe, designed to hybridise (i.e. complementary to) an mRNA sequence of interest—for example the mRNA encoding the MAPF protein c-Jun and/or CyPA, may then be used to detect and quantify the amount of a particular mRNA present in a sample. Advantageously, the results obtained may be compared with those obtained from a reference sample.

Similarly, a Southern blot may be used to detect the presence and amount of any given DNA sequence in a sample and may be used to detect the nucleic acid sequences encoding specific proteins. Briefly, nucleic acid may be extracted from a sample, subjected to a fragmentation protocol, resolved by electrophoresis and probed with a nucleic acid probe for the presence of a particular sequence. For example, the nucleic acid probe may hybridise to (i.e. complementary to) the nucleic acid sequences encoding the transcription factor, c-Jun and/or CyPA. Advantageously, the results obtained may be compared with those obtained from a reference sample.

Additionally, or alternatively, a level of a specific protein present in a sample may be identified by way of microarray analysis. Such a method would involve the use of a DNA micro-array which comprises nucleic acid derived from the genes encoding the specific protein(s). To identify the level of one or more specific proteins in a sample, one of skill in the art may extract the nucleic acid, preferably the mRNA from a sample, and subject it to an amplification protocol such as, reverse transcriptase PCR to generate cDNA. Preferably, primers specific for a certain mRNA sequence—by way of example, the sequences encoding the MAPK protein, c-Jun and/or CyPA may be used.

The amplified (for example, c-Jun and/or CyPA) cDNA may be subjected to a further amplification step, optionally in the presence of labelled nucleotides (as described above). Thereafter, the optionally labelled amplified cDNA may be contacted with the microarray under conditions which permit binding with the DNA of the microarray. In this way, it may be possible to identify a level of one or more specific proteins present in the sample tested. Advantageously, the results obtained may be compared with those obtained from a reference sample.

Further information regarding the above described techniques may be found in, for example, PCR Primer: A Laboratory Manual, Second Edition Edited by Carl W. Dieffenbach & Gabriela S. Dveksler: Cold Spring Harbour Laboratory Press and Molecular Cloning: A Laboratory Manual by Joseph Sambrook & David Russell: Cold Spring Harbour Laboratory Press.

In a second aspect there is provided a method of treating a patient having drug induced organ damage, comprising the steps of;
  (a) subjecting a sample provided by the patient to any of the methods described herein; and
  (b) administering a therapeutically effective amount of a medicament suitable for treating drug induced organ damage.

In addition, the methods provided by the present invention may be combined with existing methods in order to provide a more reliable and rapid method of identifying drug induced organ damage. For example, the present method may be combined with assays for determining the blood concentration of drugs such as paracetamol, serum transaminase enzymes (ALT and AST), blood clotting (INR) and serum creatinine.

BRIEF DESCRIPTION OF THE DRAWINGS

The present invention will now be described in detail with reference to the following figures which show.

DETAILED DESCRIPTION

Materials and Methods
Chemicals

All chemicals were obtained from Sigma (Poole, UK) unless otherwise stated.

Subjects

Healthy, male volunteers (aged 23-40, MREC ethics approval number 06/MRE00/67) were recruited from the Queen's Medical Research Institute, University of Edinburgh.

Figures 1A, 1B:
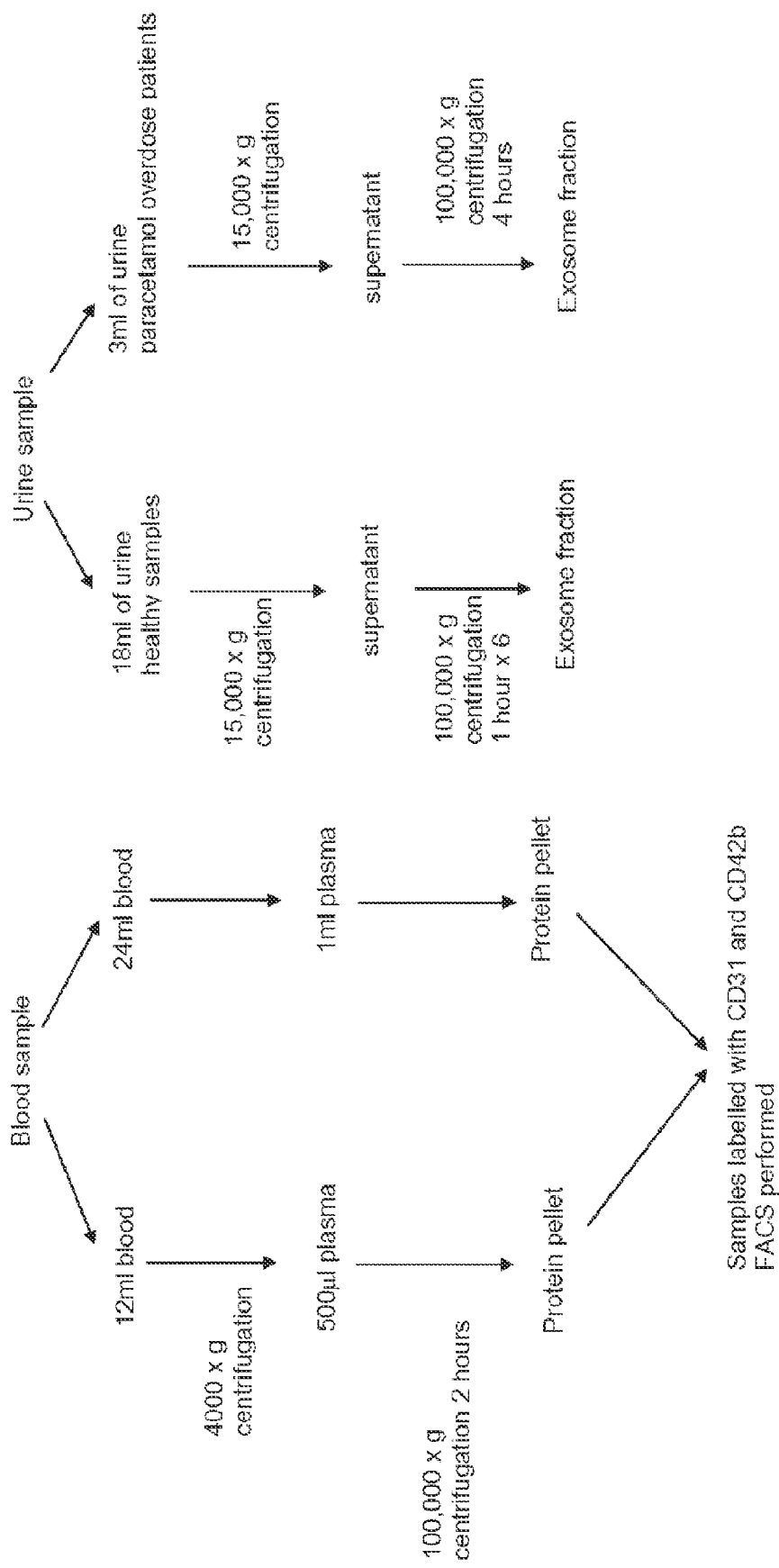
FIGS. 1A and 1B: Protocols for the isolation of microparticles from blood (A) and exosomes from urine (B).

Isolation of microparticles from human blood 12 ml (4×3 ml citrate tubes) of human blood was collected from healthy individuals. The blood was centrifuged at 4000×g for 20 minutes to separate cells from plasma. 500 μl from the top layer of the centrifuged plasma was extracted from each tube and centrifuged at 100 000 rpm (Optima™ TLX Ultracentrifuge, Beckman Coulter, Inc., USA) at 4° C. for 1 hour. The supernatant was poured off and the pellet washed twice with 1 ml saline (Braun). The pellet was resuspended in 200 μl saline and stored at 4° C. until flow cytometry analysis (see FIG. 1A).

Flow Cytometry Analysis

Flourescein isothiocyanate (FITC)-labelled anti-human CD31 and Phycoerythrin (PE)-labelled anti-human CD42b antibody markers (BD Biosciences, San Jose, USA) (20 μl antibody/100 μl MP sample) were added to the MP pellet and incubated at room temperature for 30 minutes with regular shaking. Fluorescence Activated Cell Sorting (FACS) analysis was then performed on a FACS Vantage with DiVa option (BD, San Jose, USA) in the flow cytometry core facility, QMRI, University of Edinburgh. Events were identified in forward-scatter and side-scatter intensity dot representation, gated as MPs and then plotted on one or two colour fluorescence histograms. EMPs were defined as CD31+CD42b− whilst PMPs were CD31+CD42b+.

Subjects, Urine Sample Collection and Processing

Six normal male volunteers (aged 23-40, MREC ethics approval number 06/MRE00/67) provided urine samples in sterile 50 ml plastic containers. To each urine sample a protease inhibitor was added (50:1 of 1 mM Leupeptin). Urine samples from patients who had taken an overdose of paracetamol at 4 hours and 24 hours after overdose were also analysed. 3 out of 6 of these patients had elevated serum alanine transaminase (ALT) 24 hours after admission indicating significant liver injury. The samples were centrifuged at 15000×g for 15 minutes at 4° C. to pellet the urinary sediment. The '15000×g supernatant' was then centrifuged at 100 000 rpm for 1 hour at 4° C. to obtain low density urinary exosome pellets. The 100 000 rpm supernatant was decanted and replaced with an additional '15 000×g supernatant' and ultracentrifuged again. The ultracentrifugation step was repeated 4-6 more times to harvest the exosome pellets from 18-24 ml of 15 000×g supernatant. Pellets were resuspended in 50 μl isolation solution (10 mM triethanolamine/250 mM sucrose (pH 7.6)). As there was only 3 ml of urine from the paracetamol overdose patients the protocol was altered so that 3 ml of 15 000×g supernatant was ultracentrifuged for 4 hours at 100 000 rpm to maximise the amount of urinary exosomes obtained (See FIG. 1B).

Gel Electrophoresis and Western Blotting

The amount of urine and MP protein was determined using the BCA™ Protein Assay Kit (Pierce, USA) and following the manufacturer's instructions. 20 μg of normal urine exosome samples were loaded per well. Loading amounts for each of the paracetemol overdose samples were normalised for urinary creatinine to account for differences in urine concentration. An equal amount of Laemmli Sample Buffer with 0.2M DTT (Bio-Rad) was added to the protein samples and the samples were heated at 95° C. for 5 minutes. Protein samples were separated by 1D SDS/polyacrylamide gel electrophoresis on a 12% Tris-HCl gel (Bio-rad) and run alongside molecular weight markers (Bio-Rad) at 25 mA per gel for 1 hour with migration buffer (25 mM Tris (Fisher Scientific), 192 mM glycine and 0.1% SDS).

Proteins were transferred from the gels to polyvinylidine difluoride membranes (Invitrogen) at 200 mA for 1 hour using cold transfer buffer (25 mM Tris, 192 mM glycine and 20% methanol (BDH AnalR®)). After blocking the membranes for 1 hour in 5% Skimmed Instant dried milk (Sainsbury's) in TBST (25 mM Tris-HCl, pH 8.0, 125 mM sodium chloride, 0.1% Tween 20) they were incubated overnight at 4° C. with polyclonal antibodies to GATA 2 (1:200) and c-Jun (1:200) After 3×5 minute washes in TBST the membranes were incubated with Horseradish peroxidase-conjugated secondary antibody (1:5000) for 90 minutes at room temperature. All antibodies for western blots were obtained from Santa Cruz Biotechnology, California, USA. ECL plus Western blotting detection system (Amersham Biosciences, New Jersey, USA) and light-sensitive film (Kodak) was used to visualise the antibody-antigen reactions.

Protein Gel Staining and in Gel Trypsin Digestion

Figure 6:
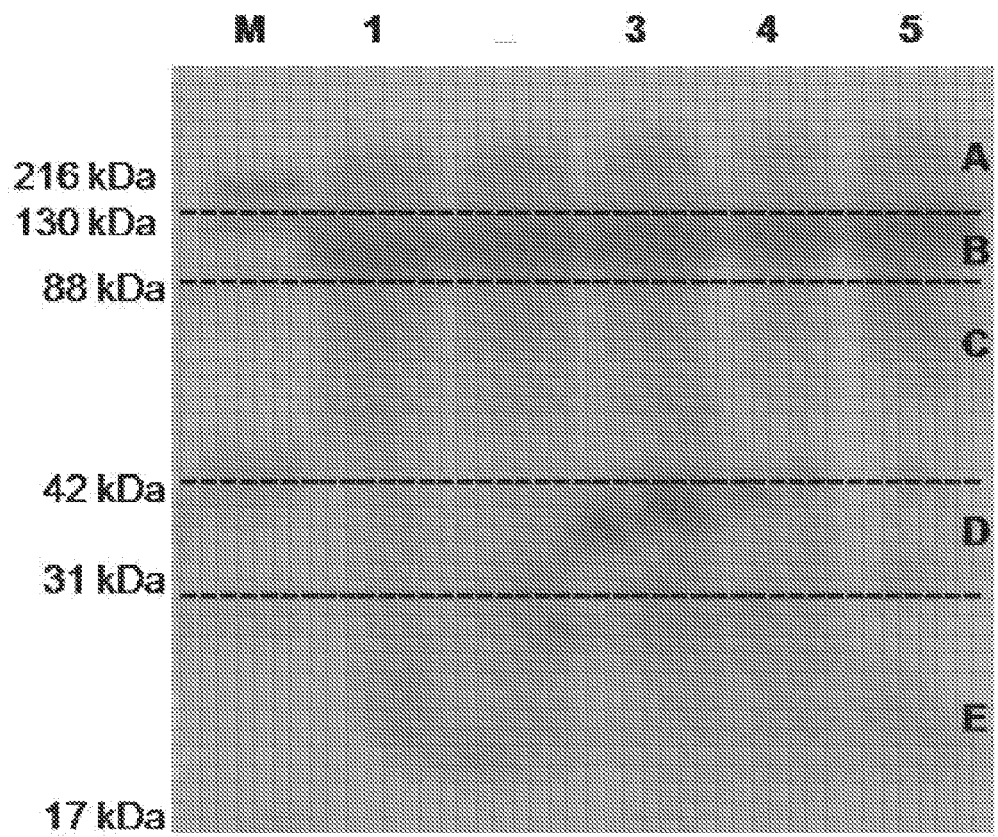
FIG. 6: Normal urine exosomal protein gel. M=molecular weight markers. Lanes 1-5 all contain ~20 μg normal urine exosome protein from the same individual. Dotted lines represent where the gel was sliced based on molecular weight markers to give five samples (A-E) for LC-MS/MS analysis.

Volumes (20 μg) of protein was loaded per well of the gel so the gel contained 100 μg protein in total and was run as before. The gel was then fixed for 1 hour in 7% glacial acetic acid and 40% methanol. The gel was stained with Colloidal Coomassie Blue for 1 hour and destained for 30 seconds in 10% glacial acetic acid and 25% methanol. The gel was rinsed with 25% methanol before being destained for 1 hour in the same solution. The gel was sliced (as shown in FIG. 6) and then sliced into smaller pieces and stored at −80° C. until the protein extraction step.

All incubations were carried out at room temperature (22° C.) with continuous shaking. The gel pieces were incubated in distilled water for 15 minutes. The water was removed and replaced by 50% acetonitrile (ACN) and incubated for 15 minutes. The ACN incubation step was repeated and the ACN was then removed and replaced with 100 mM ammonium bicarbonate (Ambic) and incubated for 5 minutes. The same volume of ACN was added to the gel pieces and incubated for a further 15 minutes. The solution was removed and the gel pieces were completely dehydrated in a speed vacuum at 60° C. The samples were then incubated with 10 mM DTT/100 mM Ambic at 56° C. for 45 minutes. The solution was removed and replaced by 55 mM iodoacetamide/100 mM Ambic and incubated at 30° C. at room temperature in the dark. The gel pieces were washed (in 100 mM Ambic) and then incubated with ACN for 15 minutes. The gel pieces were completely dehydrated in a speed vacuum. 0.1 μg/μl sequencing grade trypsin (Pierce, USA) in 1 M calcium chloride and 1 M Ambic buffer solution was added to the gel pieces and incubated at 4° C. for 45 minutes. The solution was removed and replaced with the same buffer solution but without trypsin and incubated at 37° C. overnight. The supernatant was removed and stored at 4° C. The gel pieces were incubated with 25 mM Ambic for 15 minutes and ACN was added and incubated for a further 15 minutes. The supernatant was removed and added to the overnight supernatant. The peptides were then further eluted in 5% formic acid and ACN. 10 mM DTT was added to the pooled supernatant to give a final concentration of 1 mM DTT and the supernatant dried in a speed vacuum. The samples were sent to The Chemistry Department at The King's Buildings to be analysed by LC-MS/MS.

CyPA Detection

Around 50 ml of urine was collected from patients who presented to the Royal Infirmary of Edinburgh following an APAP overdose. Urine was collected and stored at −80° C. prior to measurement of CyPA levels.

The urinary concentration of CyPA was determined by western blotting as previously described[8]. The primary antibody was rabbit anti-human cyclophilin A (USBiological, Swampscott, Mass., USA), 1:150 dilution. 100 of urine was loaded per gel lane.

Results

Flow Cytometry Analysis of MPs.

Figure 2:
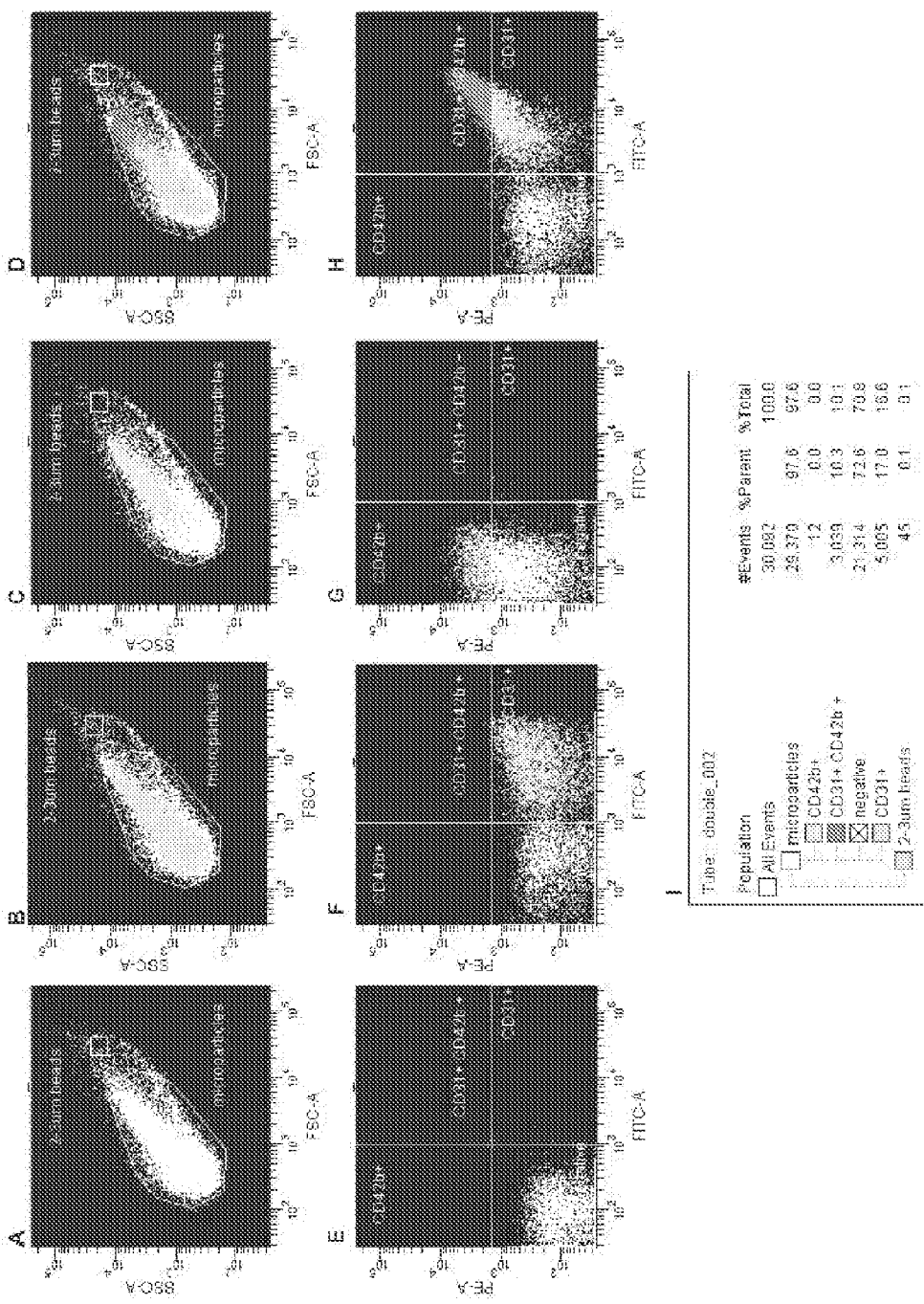
FIG. 2A-H: Representative graphs of flow cytometry analysis of circulating microparticles in plasma from normal healthy subjects. A-D Circulating MPs and calibrator beads (2.5 μm) are represented on forward scatter/side scatter dot plot histograms for unstained control, single stained FITC control, single stained PE control and double stained sorting population, respectively. E-H shows 2 parameter histograms with FITC fluorescence plotted on the x-axis and PE fluorescence on the y axis for unstained control, single stained FITC control, single stained PE control and double stained sorting population, respectively. White dots represent negative MP population; pink: single positive FITC population (CD31+/EMPs); blue: single positive PE population (CD42b+); purple: double positive population (CD31+CD42b+/PMPs). It shows the numbers of events and the percentage of each of the MP populations in the double stained sorting sample.

FIG. 2 shows the side scatter/forward scatter dot plot histograms of the samples that were sorted using FACS. The highlighted 2.5 μm calibration beads gave an indication of the size of the MPs and all the populations of MPs were below 2.5 μm in size consistent with past studies on MPs. EMPs, shown in FIG. 2 (B and F) were slightly smaller in size than PMPs, shown in FIG. 2 (C and D) as they were located below the PMP population. Singly stained MPs, either stained with CD31 or CD42b served as controls to identify the location of those populations and a sample without either cell surface marker served as a negative control and provided the number of non-endothelial- and platelet-derived MPs. The majority of MPs were negative for CD31 and CD42b and these were from differing origins and other cell types. This negative group of MPs formed a distinct population and made up 72.6% of the samples. Both EMPs and PMPs were identified as distinct populations of particles with differing size. Panels D and H show the doubly stained samples used for sorting EMPs and PMPs. There were no single positive CD42b MPs and the CD31+EMPs made up 17% whilst the CD31+ CD42b+PMPs made up 10.3% of the total MPs. The less FITC-labelled the MPs were the more likely the MPs would be endothelial in origin and only CD31+ whereas the more CD31+ the MPs were the more likely they were to also be CD42+ as well and, therefore, be platelet in origin.

Figure 3A:
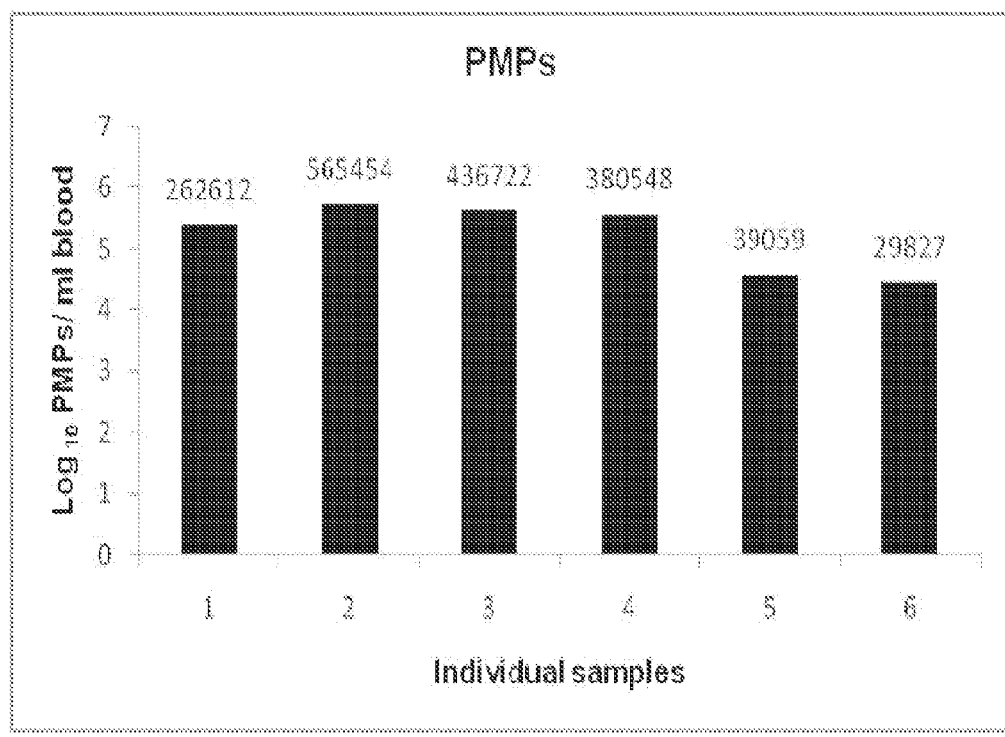
FIG. 3A&B: Microparticle numbers in healthy individual samples. The numbers of EMPs (panel B) and PMPs (panel A)/ml blood recovered by flow cytometry are shown on $\log_{10}$ graphs and the exact numbers of EMPs and PMPs for each individual are shown above each bar. There is large variability between individual samples in the numbers of MPs. Mean EMPs=1507567 (SEM 837934); mean PMPs=285704 (SEM 88864); n=6.
Figure 3B:
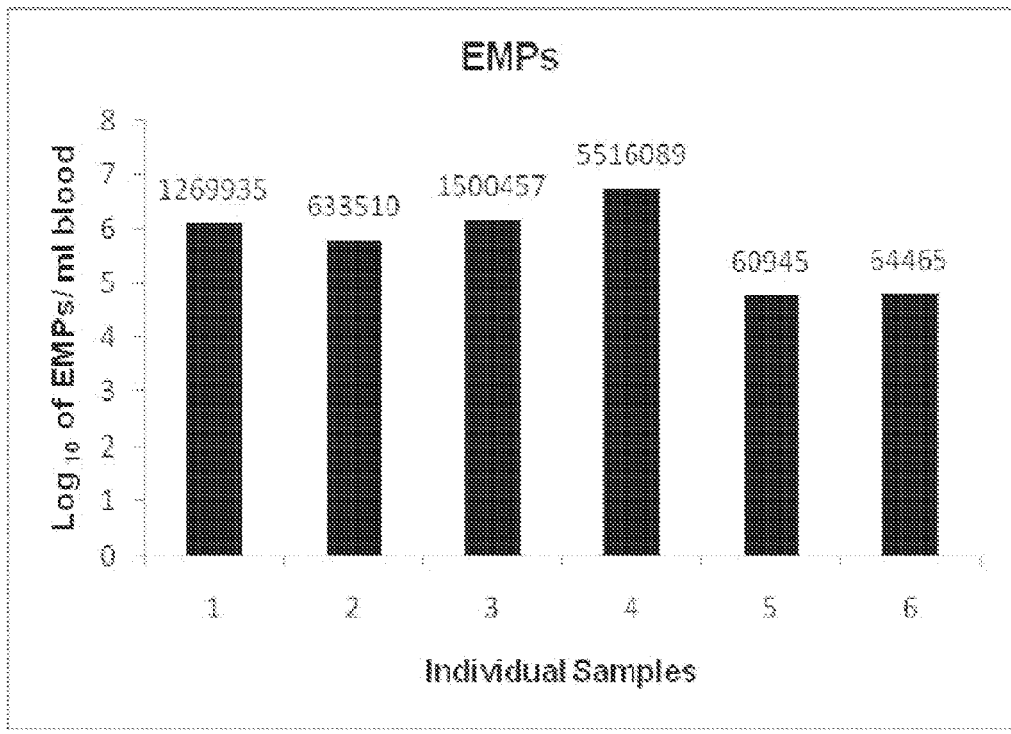

The numbers of EMPs and PMPs isolated from 6 healthy individuals showed a large amount of variability between individuals. FIG. 3 shows the $\log_{10}$ graphs of the numbers of EMPs (A) and PMPs (B) isolated during FACS. The numbers were very large and, therefore, the $\log_{10}$ gave a better graphical representation. The mean number of EMPs isolated was 1507567 (SEM 837934) whilst the mean number of PMPs isolated was 285704 (SEM 88864).

GATA-2 Protein Expression in MPs

Figure 4:
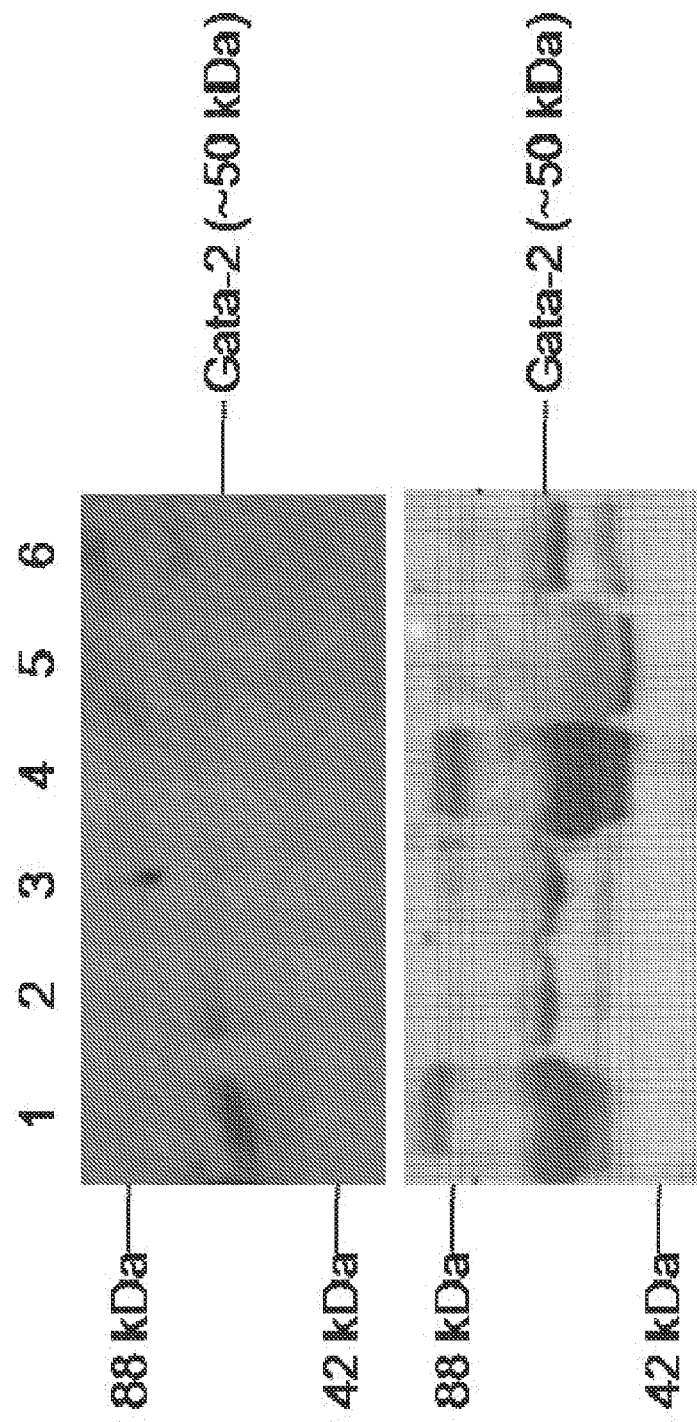
FIG. 4: Gata-2 expression in EMPs (endothelial microparticles) and PMPs (platelet microparticles). The top panel shows the western blot on the ultracentrifugation pellet whilst the bottom panel shows GATA2 (~50 kDa in size) present in the ultracentrifugation supernatant after FACS. Lane1-3: EMPs Lanes 4-6: PMPs. Lanes 1 & 4; lanes 2 & 5; lanes 3 & 6: EMPs and PMPs from the same individual.

The microparticles were investigated for the presence of the transcription factor GATA-2 by western blot. After the EMP and PMP populations were sorted the samples were ultracentrifuged to pellet the MPs. Both the pellet and supernatants after ultracentrifugation were kept and a western blot carried out to detect the presence of GATA-2. FIG. 4 shows the results of the western blot that indicated that GATA-2 was found in the supernatant and only one EMP ultracentrifuged pellet contained GATA-2. The EMP and PMP sample from individual 1 (lanes 1 and 4, respectively) had higher levels of GATA-2 than any of the other MP samples. This is consistent with the numbers of EMPs and PMPs isolated from that individual (5516089 and 380548, respectively; sample 4 in FIG. 3).

Levels of Urine Exosomes and c-Jun Expression

The exosomal protein concentration of urine in paracetamol overdose patients, both with and without organ injury was compared to normal urine. A mean of 3.54±1.22 µg protein/ml urine was found in the 6 normal urine exosomal samples. 4 hours after paracetamol overdose the pooled samples from the 3 patients that did not show organ injury had an about 7-fold increase in protein compared to normal healthy individuals. There was an ~37-fold increase in exosomal proteinuria in the pooled sample from the 3 patients with organ injury 4 hours after paracetamol overdose. 24 hours after overdose there was a decrease in the amount of exosomal protein found in the pooled urine samples for both the patients with and without organ injury to about the same levels (1.5-2 times the normal levels).

Figure 7:
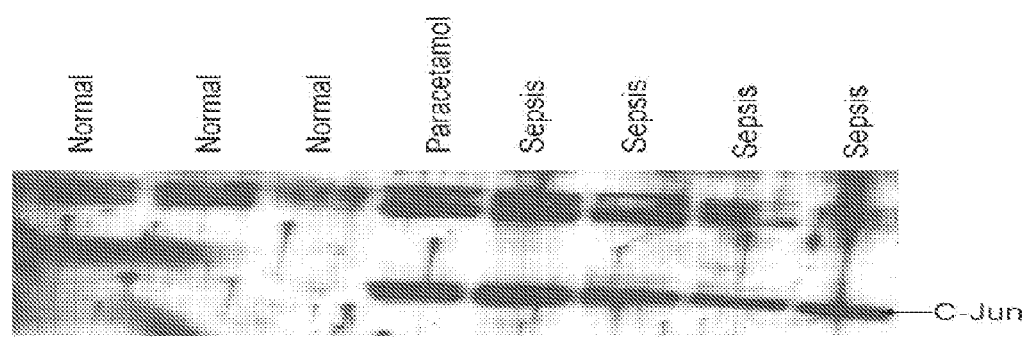
FIG. 7: Immunoblot for C-Jun. The amount of protein is increased in the urinary microparticles of patients with liver injury due to paracetamol overdose or sepsis.

In order to find if the protein c-Jun could be detected in normal urine samples and if the level of c-Jun is altered in paracetamol overdose patients a western blot was carried out. In the individual normal samples c-Jun was detected at the correct molecular weight of ~78 kDa. In addition, it was found that the urinary microparticle concentration of C-Jun protein increased following paracetamol-induced liver injury in humans (FIG. 7)

Normal Urine Exosomal Proteins

In order to perform pilot proteomics on normal urine samples ~100 µg of normal exosomes was loaded on a gel and stained with colloidal coomassie blue to show the presence of any proteins present. FIG. 6 shows the stained gel and provides evidence that there were differing sizes of proteins in the exosomal samples.

There is a protein band that appears to be the most abundant protein in the samples in section B of the gel and this is thought to be THP. The dotted lines were where the gel was cut to prepare different samples for proteomic analysis by LC-MS/MS.

EMPs as a Potential Source of Disease Biomarkers

This study sought to determine whether MPs in blood and exosomes in urine could be used as a source of potential disease biomarkers. The main findings were that whilst EMPs (endothelial microparticles) could be isolated by flow cytometry, the numbers that were isolated were highly variable between individuals (as illustrated in FIG. 3A) and the amount of protein that could be isolated was too low to be detected using standard protein assays. The isolation of MPs is also time-consuming and would not be an efficient method for a large clinical trial. One potential solution would be to perform in vitro studies on cultured endothelial cells and isolate MPs from these cultured cells. This has been carried out successfully by other groups (Combes et al., 1999). Candidate proteins could then be decided upon and their levels determined. Once potential candidate proteins had been found an in vivo study could be undertaken to determine if there were changes in the expression of these proteins in patients with organ dysfunction.

EMPs and PMPs both Show GATA-2 Expression

GATA-2 belongs to the GATA transcription factor family. GATA-2 plays an important role in hematopoietic development. Primitive hematopoietic cells express GATA-2 at high levels but during maturation of the cells into different types of blood cells the levels decline (Tsai et al., 1994). In adult endothelial cells GATA-2 is expressed and is important for the transcriptional regulation of endothelial-specific genes (Zhang et al., 1995). There are several phosphorylated forms of GATA-2 (Towatari et al., 1995) and FIG. 4 shows that there were several forms of GATA-2 in both EMPs and PMPs. However, these results need to be validated in vitro using human umbilical vein endothelial cells (HUVECS) and checking whether the same forms of GATA-2 can be detected. It is interesting observing GATA-2 in MPs as GATA-2 is a transcription factor and this raises the possibility of using transcription factors as in vivo biomarkers for gene expression.

Paracetamol Overdose Increases Exosomal Proteinuria

Figure 5A:
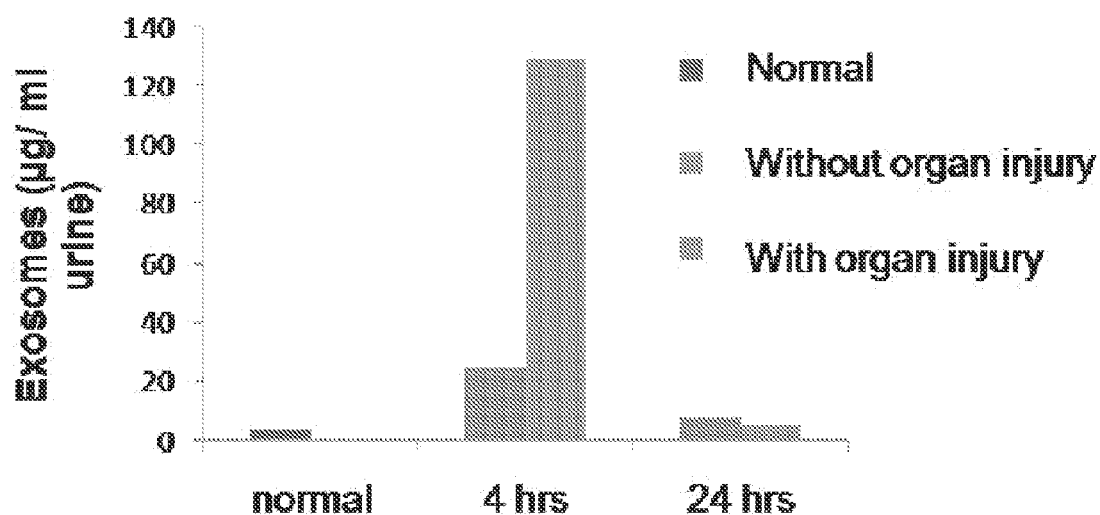
FIG. 5: Western blot for c-Jun in urine exosomes from normal subjects and paracetamol overdose patients with and without liver injury. A: protein concentration of exosomes in normal subjects (red), paracetamol overdose patients without organ injury (blue) and with organ injury (orange) 4 hours and 24 hours after overdose. B: samples from 3 normal healthy subjects showing the presence of c-Jun (~78 kDa) in the top panel and the negative control showing no c-Jun in the bottom panel.
Figure 5B:
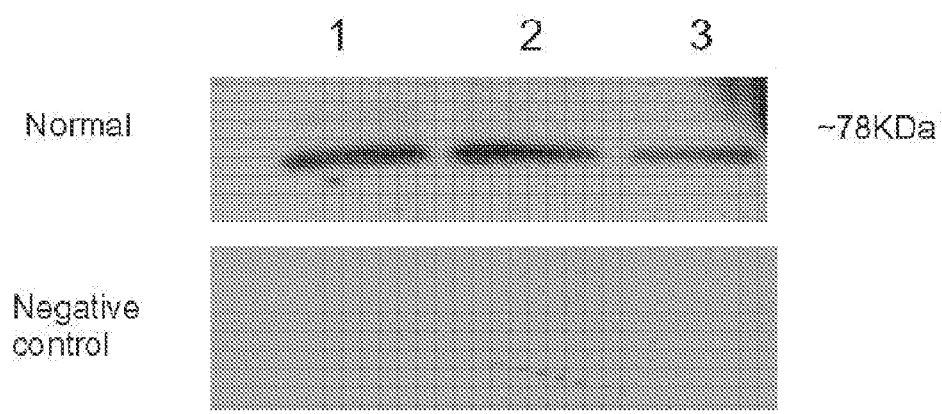

FIG. 5A shows that there was an increase in exosomal proteinuria in paracetamol overdose patients 4 hours after the overdose. The proteinuria was much higher in those patients that had suffered organ injury (~37 times as much compared to normal). The protein levels in the ultracentrifuged supernatants of overdose patients (data not shown) showed variability within the same urine samples using the same assay. This could be as a result of the presence of paracetamol metabolites in the urine as evidence exists that shows paracetamol (acetaminophen) and its metabolites can interfere with protein assays such as the BSA assay used in this study (Marshall and Williams, 1991). The exact nature of how this proteinuria occurs remains to be elucidated. It is unknown whether exosomes are released from the kidney or if the circulating MPs are passed into the urine via the glomerulus. Also whether the drug is having an effect on the kidney or the blood vessels remains to be determined. It is interesting that the proteinuria levels fall to only 1.5 times normal levels 24 hours after drug overdose but this could be explained by clinical intervention to reduce liver damage or reduced blood paracetamol concentration.

CyPA as a Marker of Drug Induced Organ Damage

Figure 8:
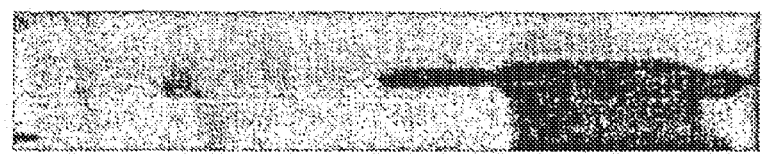
FIG. 8: Western blot for CyPA in human urine. Urine (10 μl) is from a healthy subject (A), mild liver injury secondary to APAP (B), moderate liver injury secondary to APAP (C), sever liver injury secondary to APAP (D) and liver and kidney injury secondary to APAP (E).

CyPA concentration was raised in the urine of patients with APAP-induced organ injury. FIG. 8 represents a western blot comparing urine from a healthy subject (A) with urine from patients with mild (B), moderate (C) and severe liver injury (D) and severe liver and kidney injury (E).

Figure 9:
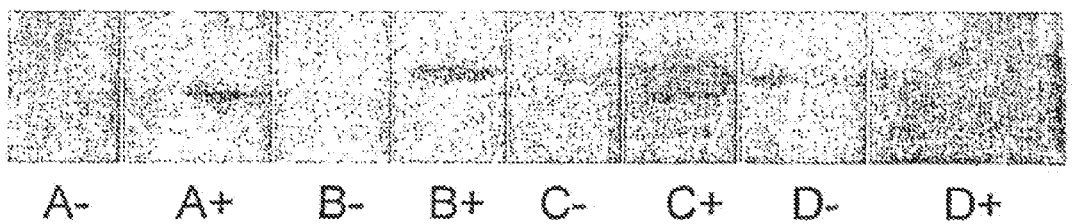
FIG. 9: Western blot for CyPA in human urine (10 μl per lane). Significant APAP-induced liver injury is indicated by +. No liver injury is indicated by −. A, B, C and D indicate age and sex matched subjects.

FIG. 9 compares urine from patients with and without APAP-induced liver injury. All the patients presented to hospital with history of APAP overdose and had APAP detectable on blood tests. The patients with liver injury are age and sex matched to a patient without injury. CyPA was raised in the urine of the patients with liver injury compared with urine from age- and sex-matched patients without injury.

The Role of c-Jun in Acute Liver Injury

Paracetamol overdose is the leading cause of acute hepatic failure in both the United Kingdom and the United States (Larson et al., 2005). The pathways linking paracetamol metabolism and liver injury have yet to be completely determined. During the early response to paracetamol overdose cytokines and chemokines are involved in both injury (Ishida et al., 2002) and repair (Hogaboam et al., 1999).

The transcription factor, c-Jun, is the major component of the AP-1 transcription factor (Bohmann et al., 1987) and a wide range of stimuli, including cellular stress, are known to induce the activity of AP-1. Exposure of cells to cytokines and environmental stresses results in the activation of the JNK group which are also known as the stress-activated proteins. Apoptosis is considered a cellular stress and, therefore, it is thought that c-Jun could be activated or up-regulated in response to apoptosis. It has been shown that JNK and c-Jun may mediate liver injury (Liu et al., 2002).

For this reason in the present study the exosomal samples obtained from paracetamol overdose patients, with and without acute liver injury, were tested for the presence of c-Jun. As a control c-Jun was detected in the samples from normal, healthy individuals and it was hypothesised that the levels of c-Jun would increase in overdose patients especially those with liver injury as they would have higher levels of apoptosis and increased c-Jun activation.

CyPA Levels Correlate with Drug Induced Organ Damage

It has been shown that CyPA is elevated in the urine of patients with liver injury secondary to APAP overdose. Accordingly, CyPA is a potential biomarker of APAP-induced liver injury. CyPA is elevated to such an extent that no normalization is required for urinary concentration and this makes it a strong potential biomarker that could be easily measured without correction for urinary creatinine. In the results presented CyPA is easily detectable in only 10 µl of urine.

CyPA is an intracellular protein that is released into the extracellular fluid in a variety of diseases in humans and animal models[5][9-11]. The mechanism of release of CyPA in APAP toxicity is unclear but, as APAP causes marked cellular necrosis, we hypothesize that leakage from injured cells is the most likely source. As extracellular CyPA is proinflammatory it may mediate the organ-injury seen in APAP toxicity.

CyPA could be a valuable clinical biomarker as it may be able to detect organ injury at a time when current markers are not yet elevated.

Proteomics as a Tool for Disease Biomarker Identification

Proteomics in the study of diseases is a useful tool and can be used for the identification of proteins in samples from diseased and non-diseased individuals. However, proteomics is not without its problems. In the present study 3 of the 5 gel slices samples that were sent for LC-MS/MS analysis could not be analysed as they contained too much colloidal coomassie blue stain. The equipment used in proteomics is highly sensitive and could be damaged by excess stain. The 2 samples that could be analysed did not appear to have any peptide fragments which is unusual. These problems can be rectified and the experiments repeated by slightly altering the protocol. The main problem of proteomics is that the highly abundant proteins, such as albumin in plasma and THP in urine, can interfere with the detection of less abundant proteins unless they are removed from the samples before proteomic analysis. THP can be removed by treating the samples with reducing agents such as DTT and re-ultracentrifugation of the samples. The THP remains in the supernatant and the pellet can be analysed for low abundance proteins (Pisitkun et al., 2004). Albumin can be removed using commercially available kits such as the SwellGel Albumin Removal kit from Pierce, Rockford, USA. An alternative is to use trichloroacetic acid and acetone to remove serum albumin (Chen et al., 2005). By removing these high abundance proteins before proteomic analysis of samples there is increased chances to identify lower abundance proteins that could provide a better idea of the body's state of health and the pathogenesis of some diseases. There have been reports of successful protein identification in MPs and exosomes. Smalley et al., (2007) were able to identify 21 proteins that were in plasma MPs and not platelet MPs and Zhou et al., (2006) identified a possible biomarker for detecting acute kidney injury.

In conclusion, the findings of this study support the idea that MPs from blood and exosomes from urine can be a potential source of disease biomarkers. Only small amounts of urine are required to obtain exosomes and this could be clinically relevant when diagnosing disease. Clinical markers that have the unique ability to indicate the onset and progression of a disease could reduce morbidity and mortality for a wide range of diseases and proteomics has an important role to play in the clinical diagnosis of diseases.

REFERENCES

Amabile, N., Guerin, A. P., Leroyer, A., Mallat, Z., Nguyen, C., Boddaert, J., London, G. M., Tedgui, A. and Boulanger, C. M. (2005). Circulating endothelial microparticles are associated with vascular dysfunction in patients with end-stage renal failure. *J Am Soc Nephrol* 16: 3381-88.

Anderson, N. L. and Anderson, N. G. (2002). The human plasma proteome: history, character, and disagnostic prospects. *Mol Cell Proteomics* 1: 845-67.

Banfi, C., Brioschi, M., Wait, R., Begum, S., Gianazza, E., Pirillo, A., Mussoni, L. and Tremoli, E. (2005). Proteome of endothelial cell-derived procoagulant microparticles. *Proteomics* 5: 4443-4455.

Bateman DN. Poisoning: focus on paracetamol. *Royal College of Physicians of Edinburgh CME* 2007; http://www.rcpe.ac.uk/fellows/CME/clin-pharmacol/bateman/bateman-2.html Bohmann, D., Bos, T. J., Admon, A., Nishimura, T., Vogt, P. K. and Tjian, R. (1987). Human proto-oncogene c-Jun encodes a DNA binding protein with structural and functional properties of transcription factor AP1. *Science* 238: 1386-1392.

Brodsky, S. V., Zhang F., Nasjletti A. and Goligorsky M. S. (2004). Endothelium-derived microparticles impair endothelial function in vitro. *Am J Physiol Heart Circ Physiol* 286: 1910-15.

Chen, Y. Y., Lin, S., Yeh, Y., Hsiao, H., Wu, C., Chen, S. and Wang, A. H. (2005). A modified protein precipitation procedure for efficient removal of albumin from serum. *Electrophoresis* 26: 2117-27.

Combes, V., Simon, A. C., Grau, G. E., Arnoux, D., Camoin, L., Sabatier, F., Mutin, M., Sanmarco, M., Sampol, J. and Dignat-George, F. (1999). In vitro generation of endothelial microparticles and possible prothrombotic activity in patients with lupus anticoagulant. *J Clin Invest* 104: 93-102.

George, J. N., Thoi, L. L., McManus, L. M. and Reimann, T. A. (1982). Isolation of human platelet microparticles from plasma and serum. *Blood* 60: 834-840.

Henderson, N. C., Pollock, K., Frew, J., Mackinnon, A. C., Flavell, R. A., Davis, R. J., Sethi, T. and Simpson, K. J. (2006). Critical role of c-jun (NH2) terminal kinase in paracetamol-induced acute liver failure. *Gut* (E-pub ahead of print).

Hewitt, S. M., Dear, J. W., Star, R. A. (2004). Discovery of protein biomarkers for renal diseases. *J Am Soc Nephrol* 15: 1677-89.

Hogaboam, C. M., Simpson, K. J., Chensue, S. W., Steinhauser, M. L., Lukacs, N. W., Gauldie, J., Strieter, R. M. and Kunkel, S. L. (1999). Macrophage inflammatory protein-2 gene therapy attenuates adenovirus- and paracetamol-mediated hepatic injury. *Gene Ther* 6: 573-584.

Ishida, Y., Kondo, T., Ohshima, T., Fujiwara, H., Iwakura, Y. and Mukaida, N. (2002). A pivotal involvement of IFN-gamma in the pathogenesis of paracetamol-induced acute liver injury. *FASEB J* 16:1227-1236.

Johnstone, R. M., Adam, M., Hammond, J. R., Orr, L. and Turbide, C. (1987). Vesicle formation during reticulocyte maturation. Association of plasma membrane activities with released vesicles (exosomes). *J Biol Chem* 262: 9412-20.

Larson, A. M., Polson, J., Fontana, R. J., Davern, T. J., Lalani, E., Hynan, L. S., Reisch, J. S., Schiodt, F. V., Ostapowicz, G., Shakil, A. O. and Lee, W. M. (2005). Acetaminophen-induced acute liver failure: results of a United States multicenter, prospective study. *Hepatology* 42 (6): 1364-72.

Liu, H., Lo, C. R. and Czaja, M. J. (2002). NF-kappaB inhibition sensitizes hepatocytes to TNF-induced apoptosis through a sustained activation of JNK and c-Jun. *Hepatology* 35:772-778.

Marshall, T. and Williams, K. M. (1991). Drug interference in the Bradford and 2,2'-bicinchoninic acid protein assays. *Anal Biochem* 198: 352-4.

Pisitkun, T., Shen, R. F. and Knepper, M. A. (2004). Identification and proteomic profiling of exosomes in human urine. *Proc Natl Acad Sci USA* 101: 13368-73.

Preston, R. A., Jy, W., Jimenez, J. J., Mauro, L. M., Horstman, L. L., Valle, M., Aime, G. and Ahn, Y. (2003). Effects of severe hypertension on endothelial and platelet microparticles. *Hypertension* 41: 211-217.

Reilly T P, Bourdi M, Brady J N, Pise-Masison C A, Radonovich M F, George J W, et al. Expression profiling of acetaminophen liver toxicity in mice using microarray technology. *Biochem Biophys Res Commun* 2001; 282(1): 321-8

Smalley, D. M., Root, K. E., Cho, H., Ross, M. M. and Ley, K. (2007). Proteomic discovery of 21 proteins expressed in human plasma-derived but not platelet-derived microparticles. *Thromb Haemost* 97: 67-80.

Towatari, M., May, G. E., Marais, R., Perkins, G. R., Marshall, C. J., Cowley, S. and Enver, T (1995). Regulation of GATA-2 Phosphorylation by Mitogen-activated Protein Kinase and Interleukin-3. *J Biol Chem* 270: 4101-4107.

Tsai, F. Y., Keller, G., Kuo, F. C., Weiss, M., Chen, J., Rosenblatt, M., Alt, F. W. and Orkin, S. H. (1994). An early haematopoietic defect in mice lacking the transcription factor GATA-2. *Nature* 371: 221-226.

Wolf, P. (1967). The nature and significance of platelet products in human plasma. *Br J Haematol* 3: 269-88.

Zhang, R., Min, W. and Sessa, W. C. (1995). Functional analysis of the human endothelial nitric oxide synthase promoter: Sp1 and GATA factors are necessary for basal transcription in endothelial cells. *J Biol Chem.* 270: 15320-15326.

Zhou, H., Yuen, P. S. T., Pisitkun, T., Gonzales, P. A., Yasuda, H., Dear, J. W., Gross, P., Knepper, M. A. and Star, R. A. (2006). Collection, storage, preservation and normalisation of human urinary exosomes for biomarker discovery. *Kidney International* 69: 1471-76.

Zhou, H., Pisitkun, T., Aponte, A., Yuen, P. S, T., Hoffert, J. D., Yasuda, H., Hu, X., Chawla, L., Shen, R. F., Knepper, M. A. and Star, R. A. (2006). Exosomal Fetuin-A identified by proteomics: A novel urinary biomarker for detecting acute kidney injury. *Kidney International* 70: 1847-1857.

ADDITIONAL REFERENCES

Referenced by Number in Text

1. Waring W S, Stephen A F, Robinson O D, Dow M A, Pettie J M. Lower incidence of anaphylactoid reactions to N-acetylcysteine in patients with high acetaminophen concentrations after overdose. *Clinical Toxicology* 2008; 46(6): 496-500.
2. Colgan J, Asmal M, Yu B, Luban J. Cyclophilin A-Deficient Mice Are Resistant to Immunosuppression by Cyclosporine. *J Immunol* 2005; 174(10): 6030-6038.
3. Takahashi N, Hayano T, Suzuki M. Peptidyl-prolyl cis-trans isomerase is the cyclosporin A-binding protein cyclophilin. *Nature* 1989; 337(6206): 473-5.
4. Luban J, Bossolt K L, Franke E K, Kalpana G V, Goff S P. Human immunodeficiency virus type 1 Gag protein binds to cyclophilins A and B. *Cell* 1993; 73(6):1067-78.
5. Arora K, Gwinn W M, Bower M A, Watson A, Okwumabua I, MacDonald H R, et al. Extracellular cyclophilins contribute to the regulation of inflammatory responses. *J Immunol* 2005; 175(0:517-22.
6. Yurchenko V, Constant S, Bukrinsky M. Dealing with the family: CD 147 interactions with cyclophilins. *Immunology* 2006; 117(3):301-9.
7. Dear J W, Leelahavanichkul A, Aponte A, Hu X, Constant S L, Hewitt S M, et al. Liver proteomics for therapeutic drug discovery: Inhibition of the cyclophilin receptor CD147 attenuates sepsis-induced acute renal failure*. *Crit Care Med* 2007; 35(10):2319-2329.
8. Holly M K, Dear J W, Hu X, Schechter A N, Gladwin M T, Hewitt S M, et al. Biomarker and drug-target discovery using proteomics in a new rat model of sepsis-induced acute renal failure. *Kidney Int* 2006; 70(3):496-506.
9. Gwinn W M, Damsker J M, Falahati R, Okwumabua I, Kelly-Welch A, Keegan A D, et al. Novel approach to inhibit asthma-mediated lung inflammation using anti-CD 147 intervention. *J Immunol* 2006; 177(7):4870-9.
10. Billich A, Winkler G, Aschauer H, Rot A, Peichl P. Presence of Cyclophilin A in Synovial Fluids of Patients with Rheumatoid Arthritis. *J. Exp. Med.* 1997; 185(5):975-980.
11. Tegeder I, Schumacher A, John S, Geiger H, Geisslinger G, Bang H, et al. Elevated serum cyclophilin levels in patients with severe sepsis. *J Clin Immunol* 1997; 17(5): 380-6.

The invention claimed is:

1. A method of identifying whether a patient has, or is at risk of developing drug induced liver damage, said method comprising the steps of;
   (a) providing a sample from a patient; and
   (b) identifying a level of cyclophilin A (CypA) protein in said sample;
   wherein an increase in the level of protein indicates that the patient has, or is at risk of developing drug induced liver damage.

2. The method of claim 1, wherein the liver damage is induced by one or more antibiotics and/or anti-inflammatory, antipyretic, analgesic and/or chemotherapeutic agents.

3. The method of claim 1, wherein the liver damage is induced by paracetamol (N-(4-hydroxyphenyl)ethanamide).

4. The method of claim 1, wherein the sample is a tissue sample, biopsy and/or a body fluid selected from whole blood, plasma, serum, lymph, urine, sweat, saliva and tissue and/or gland secretions.

5. The method of claim 1, wherein the sample is urine.

6. The method of claim 1, wherein the sample is subjected to a protocol capable of isolating microparticles and/or exosomes therefrom.

7. The method of claim 1, further comprising the step of comparing the level of protein identified with a level of the same protein identified in a control or reference sample.

8. The method of claim 7, wherein the reference or control sample is subjected to a microparticle/exosome isolation protocol.

9. The method of claim 1, wherein the step of identifying a level of protein in a sample, further comprises the identification of levels of nucleic acids present in the sample provided.

10. The method of claim 1, wherein the step of identifying a level of protein in a sample comprises an immunological technique.

11. The method of claim 9, wherein the nucleic acids encode the transcription factor c-Jun or CypA.

12. A method of identifying whether a patient has, or is at risk of developing paracetamol induced liver damage, said method comprising the steps of:

(a) providing a sample from a patient; and
(b) identifying a level of CypA protein in said sample;
   wherein an increase in the level of CypA protein indicates that the patient has or is at risk of developing, paracetamol induced liver damage.

13. The method of claim 1 or claim 12, comprising the further step of detecting a level of the transcription factor c-Jun-N-terminal kinase (JNK) in said sample.

* * * * *